US008002797B2

(12) United States Patent
Mayer

(10) Patent No.: US 8,002,797 B2

(45) Date of Patent: Aug. 23, 2011

(54) THERAPEUTIC, TILTING, SPLIT TABLE, TRACTION APPARATUS

(76) Inventor: Zoltan Joseph Mayer, Royal Palm Beach, FL (US)

( * ) Notice: Subject to any disclaimer, the term of this patent is extended or adjusted under 35 U.S.C. 154(b) by 825 days.

(21) Appl. No.: 12/077,522

(22) Filed: Mar. 20, 2008

(65) Prior Publication Data

US 2009/0240282 A1 Sep. 24, 2009

(51) Int. Cl.
*A61F 5/00* (2006.01)

(52) U.S. Cl. ............. 606/241; 606/244; 602/32; 602/33

(58) Field of Classification Search .................. 606/237, 606/241-245; 602/32-36; 601/23, 24, 26; 482/112, 113, 142; 5/612, 618, 658, 662

See application file for complete search history.

(56) References Cited

U.S. PATENT DOCUMENTS 4,103,681 A * 8/1978 Shanley ........................ 606/244
4,419,989 A * 12/1983 Herbold ........................ 606/242
6,277,141 B1 * 8/2001 Lake ............................ 606/243

* cited by examiner

*Primary Examiner* — Quang D Thanh

(57) ABSTRACT

A therapeutic, tilting, split table, traction apparatus for home use manually operated by the user to relieve back pain and/or to stretch lumbar spine and exercise back muscles and provide mechanical traction with the user in supine position. The apparatus having a upper tilting frame, one end being back and head support and opposing end being a rolling or sliding carriage, pivotally hinged on base frame with approximately 13 kilograms of upper body weight offset unto the back support to offset the effect of the 13 kilogram spring used to retract the rolling or sliding carriage and keep body weight balanced for ease of use. Lower body is anchored by pelvic or waist harness to the rolling or sliding carriage. As the user releases latch, the frame tilts and simultaneously pushes up a rod and roller assembly, which is hinged to under back support and under rolling carriage, along the 35 degree incline track thereby pushing carriage away from back support creating traction/distraction force. Removable handles attached to base are used by the user to control tilt and traction force.

1 Claim, 2 Drawing Sheets

THERAPEUTIC, TILTING, SPLIT TABLE, TRACTION APPARATUS

BACKGROUND OF THE INVENTION

This invention relates broadly to traction tables for treating back pain and other back problems. More specifically the invention is directed towards incline and tilting tables manually operated by the patient for home use.

Various therapeutic traction devises are known in the art. By way of example U.S. Pat. No. 4,103,681 describes a table that tilts to provide traction using a material between persons back and vinyl surface of table to reduce friction, while tilting, with legs over end of table and a waist harness as an anchor to apply traction force.

The prior art does not address proper breathing and relaxing back muscles to facilitate distraction in vertebrae and furthermore the art does not address stretching and/or traction/distraction as a preventative measure for back problems.

There is a need in the art to provide a therapeutic traction devise that is easy for a person to use at home or anywhere and can provide controlled mechanical traction for back pain as well as stretch back muscles as a preventative measure for back problems, with amount of force easily controlled by user, applied, intermittently, using an on-off cycle, or continuously.

The present invention overcomes problems associated with the prior art in that it uses the vinyl surface as an advantage, as the persons back sticking to the back support vinyl is anchoring upper body. Lower body is anchored to rolling or sliding carriage by way of pelvic harness. Simultaneous action of tilting, and carriage moving away from back support cause traction/distraction force with little effort of person, applied, intermittently, using an on-off cycle, or continuously. Further addressing method of breathing and relaxing back muscles during traction/distraction to effect vertebral distraction.

SUMMARY OF THE INVENTION

The present invention, a Therapeutic, tilting, split table, traction apparatus, platform/upper frame split in two sections pivotally hinged on a base frame. The table is self operated lying in supine position and easy to use by the person at home, office or work place, to stretch lower back muscles, before and/or after athletic activity or bending or lifting type work as preventative measure. Or use as therapy for back pain by applying traction/distraction to lumbar region or spine The platform or upper frame consists of two sections, back support, and buttocks, adjustable knee and foot support mounted to a rolling or sliding carriage Base or lower frame consisting of roller assembly with two rods, one rod end hinged to roller assembly, opposite end hinged to bottom of back support. Second rod is hinged to same roller assembly and opposite end hinged to bottom of rolling or sliding carriage. As person releases latch (to keep frame in locked horizontal position) upper frame tilts down (head below feet) pushing rod pushing roller assembly up a track (angled at thirty five degrees) which pushes rolling or sliding carriage away from back support to produce approximately 15 cm of separation between back support and rolling or sliding carriage providing traction/distraction force. Body support surfaces covered with foam padded vinyl knees are supported mainly by feet resting on adjustable platform with knees supported by way of adjustable knee support that moves up and down and forward and backward with side rails (to keep knees from sliding sideways off support) hinged on the carriage so you can adjust legs approximately sixty to ninety degrees to provide a comfortable angle for traction/distraction. Base frame has removable handles that person uses to control the amount of incline or tilt and traction force by; holding onto handles then releasing the latch letting the table incline with head going lower then the feet.

Person is restrained by way of pelvic/waist harness and adjustable straps attached to rolling carriage. Persons back and head rest on the back support. Although a person can be clothed while using apparatus the preferred method is with skin on back in direct contact with vinyl on back support causing persons back to stick to the vinyl increasing the traction force. Using the handles with hands and arms to control the tilt or drop of the apparatus, person also controls the desired time and traction force based on comfort and able to control, traction/distraction force intermittently, using an on-off cycle, or continuously.

Preferred method of operation is; release latch while holding unto handles with both hands letting yourself down slowly while breathing out, relax and then pull yourself up while breathing in, relax and repeat. As person feels muscles in back loosen or after a few minuets, person can spend as much time as comfortable at partial or full incline position, while concentrating on shallow breathing pushing out as much air as possible from the pelvic region and then pull self back to horizontal position and relax, repeat as comfortable.

BRIEF DESCRIPTION OF VIEWS OF DRAWINGS

DETAILED DESCRIPTION OF THE INVENTION

The present invention will be described fully with reference to the accompanying drawings in witch preferred embodiments of the invention are shown. This invention may, however, be embodied in many different forms and should not be construed as limited by the embodiments set forth herein. Rather, these embodiments are provided so that this disclosure will be through and complete, and will fully convey the scope of the invention to those skilled in the art.

Figure 1:
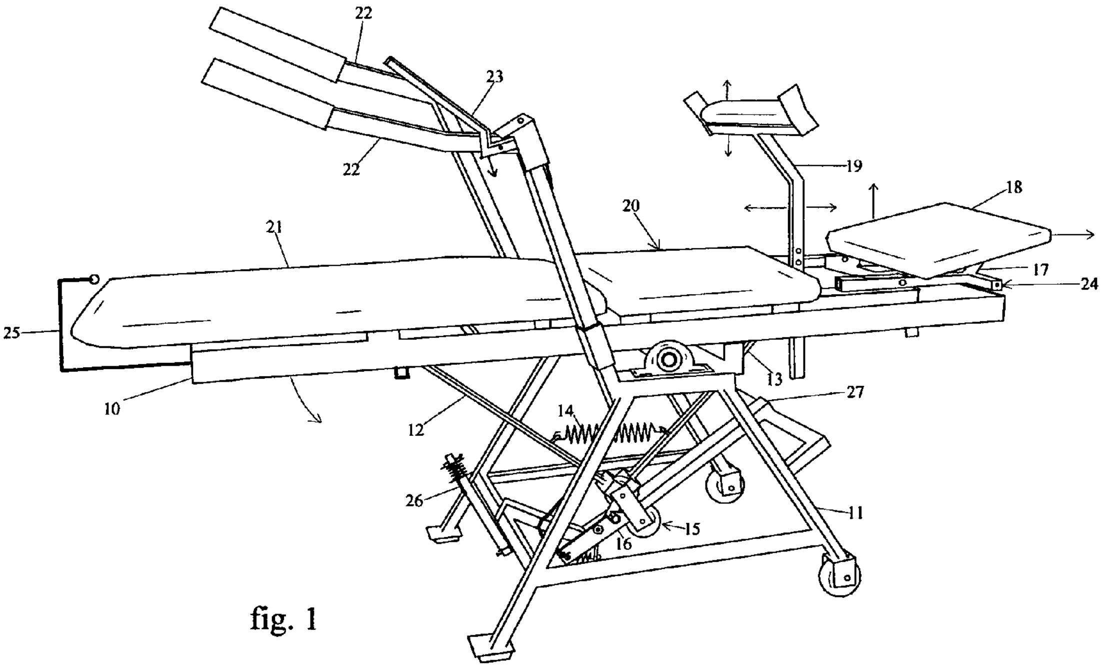
FIG. 1 is a perspective view of Therapeutic, tilting, split table, traction apparatus incorporating my present invention, being the preferred embodiment.
Figure 2:
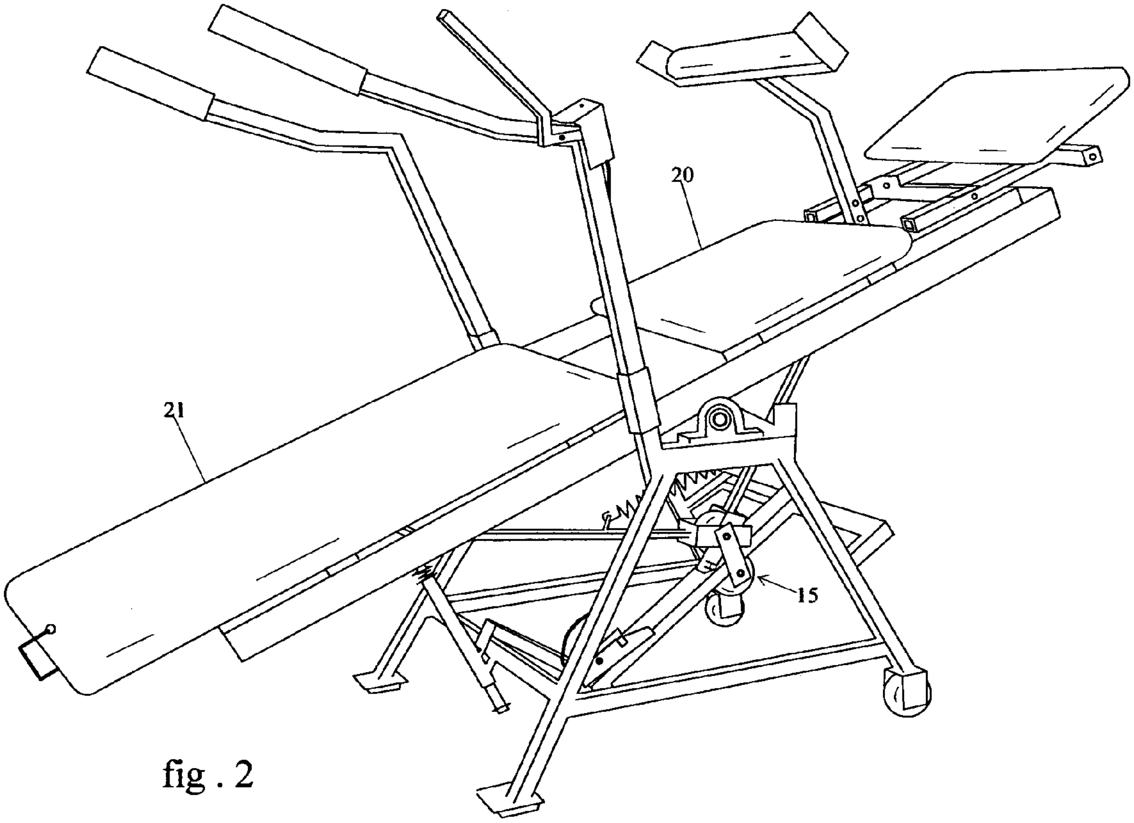
FIG. 2 is a perspective view of Therapeutic, tilting, split table, traction apparatus in the tilted or inclined position to illustrate the apparatus as preferred embodiment of the present invention.

Referring to the drawing, wherein like numerals represent like parts throughout the drawings. A preferred embodiment of the present invention FIG. 1 shows the Therapeutic tilting split table traction apparatus consisting of upper frame 10 made from metal angle iron with padded vinyl back support, hinged and pivotally balanced on lower base frame 11, made from metal square tubing, metal angle iron and metal U channel track 27, although it can be made with different metals and or tubing, welded and/or bolted together. Persons lower body, waist down is anchored on rolling or sliding carriage unit 20 also metal square tubing, and flat metal with padded vinyl, carriage 20 is positioned on frame past the balance point with more of persons body weight about thirteen kilograms going unto the back support. Main weight of legs are on feet, resting on foot pad 18 that is hinged to adjustable foot support 17 to move in way designated by direction of arrows, with side rails on 19 keeping knees from falling to the side. The carriage unit 20 is riding on wheels hidden behind frame 10 and comprising of 19, knee support, 18, foot rest and 17, foot support, so your lower body rests on the movable carriage. The carriage can also be made to slide. The pelvic or waist harness (not shown) attaches to the carriage 20 at point 24 as designated by the arrow with an adjustable strap that person pulls to take up slack. With the waist portion of pelvic harness positioned were table splits. Person laying on table with legs in comfortable position or approximately 60 to 90 degrees with your back against back support 21 with pelvic harness attached. Although you can be clothed the preferred method is to have your skin on back in direct contact with padded vinyl causing person to stick to vinyl anchoring back. The supporting surfaces are covered in foam padded vinyl. Holding unto handles 22, pull release lever 23 connected by cable to latch 16, you should feel a slight drop as upper frame 10 tilts down with head being below feet. Rod 12, hinged under approximate center of back support and opposing end hinged to roller assembly 15. Rod 13 that is also hinged to roller assembly 15 and hinged under approximate center of rolling or sliding carriage 20. As person releases lever 23 frame 10 tilts down simultaneously moving roller assembly 15 up track 27 angled at approximately thirty five degrees causing carriage 20 to roll or slide away or separate from back support 21 creating a distance of approximately fifteen cm (at full incline) between back support 21 and rolling or sliding carriage 20, thus creating enough distraction force. Persons upper body is anchored to the back support by way of back sticking to vinyl surface of back support. Lower body is anchored to carriage 20 creating 15 cm distance between lower body and upper body minus slippage. Roller assembly 15 has two wheels one riding on top of track 27 and one riding below track 27, wheels are hinged together to keep roller assembly 15 on track as frame 10 returns from incline to horizontal position. Spring stop 26 hits bottom of frame when in full incline to avoid abrupt stop. Spring 14 is attached to rod 12 and rod 13. Spring force is approximately 13 kilograms to counterweight approximately 13 kilograms of body weight offset unto back support.

This spring action between rods 12 and 13 expands at incline or tilt as carriage moves away and retracts as you pull up to horizontal position, also retracting rolling carriage, thus aiding in balancing body weight, so you need very little energy to pull back up to horizontal position.

As a means of stretching spine a optional head harness with chin strap (not shown) can be used attached to sliding adjustable bracket 25.

In another embodiment Therapeutic tilting split table traction apparatus can use a electric or hydraulic linier actuator with remote control, (not shown) replacing 26 spring stop and hinged to under upper frame 10 and opposing end hinged to frame 11. Using remote to lower and raise upper frame without using handles to control traction force and time at tilt positions.

That which is claimed is:

1. A therapeutic tilting split table traction apparatus useful in the treatment of back pain and stretching back muscles as a preventative measure against back problems, the apparatus comprising:

an upper frame pivotally hinged to a base frame;

wherein the upper frame comprising: a back and head support having supporting surface covered with foam padded vinyl for anchoring an upper body of a person at one end of the upper frame, and a rolling or sliding carriage disposed at an opposite end of the upper frame, wherein the rolling or sliding carriage supports buttocks, knees and feet of the person and has attach point for a pelvic harness; a knee support that is adjustable up and down and back and forth to fit a height of the person and keep the person's legs in a comfortable incline position of approximately sixty to ninety degrees, the knee support having side rails to keep the knees from falling to a side and a foot support for supporting the legs such that there having no pressure under the knees aiding in relaxing a lower body of the person;

wherein the base frame comprising: a first rod having one end hinged to the upper frame under approximate a center of the back and head support and an opposing end hinged to a roller assembly, a second rod having one end hinged to under approximate a center of the rolling or sliding carriage and an opposing end hinged to the roller assembly, such that when the upper frame tilts down with the person's head lower than the feet, the first rod connecting from the back and head support simultaneously moves the roller assembly upward along a track having an angle of inclination approximately thirty five degrees and pushes the rolling or sliding carriage with the lower body anchored to it, by way of the pelvic harness, away from the back and head support creating approximately fifteen cm of space between the back and head support and the rolling or sliding carriage at full incline thereby creating a traction/distraction force;

removable handles are provided to allow the person to hold unto the handles to lower and raise the upper frame thereby controlling tilt and traction/distraction force, wherein traction/distraction can be applied intermittently using an on-off cycle, or continuously with little effort from the person; and an electric or hydraulic linear actuator with remote control to lower and raise the upper frame without using the handles to control tilt and traction/distraction force, the actuator having one end hinged to under the back and head support of the upper frame and an opposing end hinged to the base frame; and wherein traction/distraction can be applied to the person's lumbar region by way of person's back anchored to the back and head support and the lower body anchored to the rolling or sliding carriage.

* * * * *